US00PP17142P2

(12) United States Plant Patent
Lemon

(10) Patent No.: US PP17,142 P2
(45) Date of Patent: Oct. 10, 2006

(54) ***GERANIUM* PLANT NAMED 'ELEGANCE BURGUNDY'**

(50) Latin Name: *Pelargonium domesticum*
Varietal Denomination: Elegance Burgundy

(75) Inventor: David G. Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 11/177,058

(22) Filed: Jul. 8, 2005

(51) Int. Cl.
*A01H 5/00* (2006.01)

(52) U.S. Cl. ..... Plt./331

(58) Field of Classification Search ..... Plt./331
See application file for complete search history.

*Primary Examiner*—Kent Bell
(74) *Attorney, Agent, or Firm*—The Webb Law Firm

(57) ABSTRACT

'Elegance Burgundy' is a new variety of *geranium* that exhibits free flowering and satiny, deep burgundy flowers.

1 Drawing Sheet

Botanical classification: *Pelargonium domesticum.*
Varietal denomination: 'Elegance Burgundy'.

BACKGROUND OF THE INVENTION

The present invention comprises a new and distinct cultivar of *Pelargonium domesticum* known by the varietal name 'Elegance Burgundy'. The new variety was discovered in Lompoc, Calif. The new variety is a result of cross breeding Orchid Seedling #4390 (female parent) (unpatented) and Lavender Seedling #3020 (male parent) (unpatented). The purpose of the breeding program was to introduce new regal *geraniums* that are less sensitive to light and temperature. The new variety is similar in plant type to its female parent and has a deeper flower color than both parents. The new variety is free flowering like its male parent. 'Elegance Burgundy' is similar in flower color and easy to root like 'Dapper Burgundy', but is earlier to flower. 'Elegance Burgundy' is also very free flowering and exhibits an excellent flower color when compared to other varieties known to the breeder. The new variety was first asexually reproduced by cuttings in Connellsville, Pa. The new variety has been trial and field tested and has been found to retain its distinctive characteristics and remain true to type through successive propagations.

The new variety was grown in a glass greenhouse in a 5" pot in Connellsville, Pa. using full light, 16° C. night temperature, 20° C. day temperature, and grown in a soilless media with constant fertilizer at 200 ppm nitrogen and potassium. The new variety was grown under 16-hour days with supplemental high pressure sodium lamps. The new variety exhibits developed roots at 24–26 days at an average temperature of 21° C. and has a response time of fifteen weeks from a rooted cutting to flowering in a 12.7 cm. container.

DESCRIPTION OF THE DRAWING

The accompanying photographic drawing illustrates the new variety, with the color being as nearly true as is possible with color illustrations of this type.

DESCRIPTION OF THE PLANT

Figure 1:
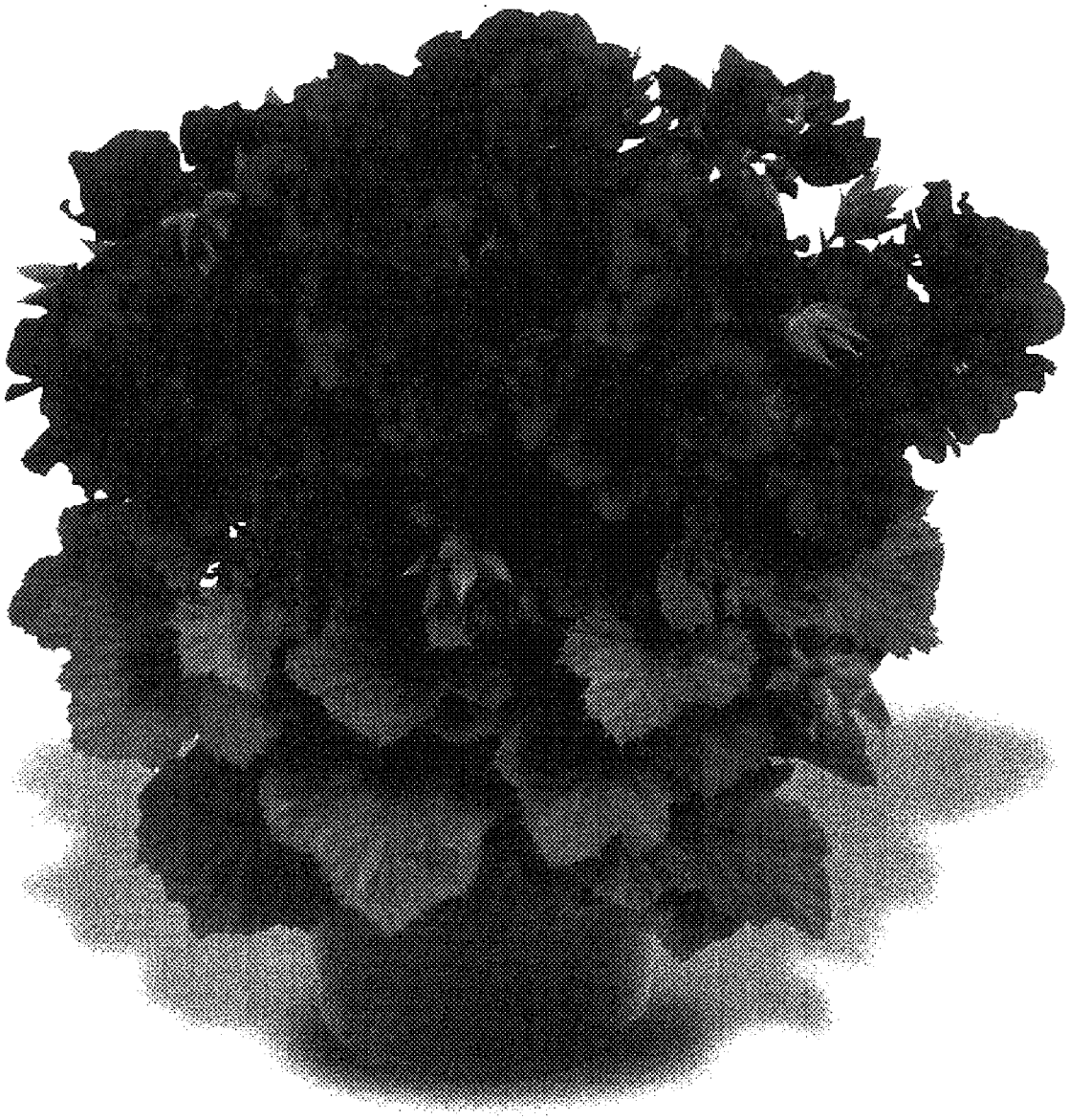

The following detailed description sets forth the characteristics of the new cultivar. The data which defines these characteristics were collected by asexual reproductions carried out in Connellsville, Pa. The color readings were taken indoors under 65–85 foot candles of cool white fluorescent light. The new variety was fifteen weeks from a rooted cutting when described. Color references are primarily to the 1966 R.H.S. Colour Chart of The Royal Horticultural Society of London.

PLANT

Market class: Regal.
Time to initiate roots: About 12–14 days at about 21° C.
Time to develop roots: About 24–26 days at about 21° C.
Time to produce a finished flowering plant from a rooted cutting: About 15 weeks in a 12.7 cm. container.
Rooting habit: Good, normal.
Form: Round-mounded.
Height from media surface to top of foliage: 18–19 cm.
Height from media surface to top of flowers: 25.0–28.0 cm.
Plant diameter: 24.0–25.0 cm.
Strength: No artificial support is needed.
Branching habit: Well branched.
Stem:
- *Main stem length.*—18 cm.
- *Diameter.*—1 cm.
- *Color.*—Yellow-green Group 144A.
- *Texture.*—Leathery texture.
- *Pubescence.*—Present.
- *Internode length.*—2.0 cm.

Lateral branches:
- *Length.*—Primary: 7.0–9.0 cm. Secondary: Plant is too young to measure.
- *Diameter.*—Primary: 0.5 cm. Secondary: Plant is too young to measure.
- *Internode length.*—2.0 cm.
- *Texture.*—Leathery texture.
- *Pubescence.*—Present.
- *Color.*—Yellow-Green Group 144A.

Foliage:

*Arrangement.*—The first set of leaves is opposite, the following leaves are alternate in arrangement.

*Stipules.*—Size: 1.5 cm. high by 1.0 cm. wide. Color: Yellow-Green Group 144A.

*Zone.*—None present.

*Size of leaf.*—Length: 5.2–7.3 cm. Width: 5.5–8.0 cm.

*Shape of leaf* (*generally*).—Reniform.

*Shape of apex.*—Pointed.

*Shape of base.*—Truncate.

*Texture.*—Leathery.

*Margin type.*—Serrated, lobed.

*Pubescence.*—Upper surface: Moderate. Lower surface: Moderate.

*Color.*—Young leaves: Upper surface: Green Group 143A. Lower surface: Green Group 138B. Mature leaves: Upper surface: Green Group 137A. Lower surface: Green Group 137C.

*Petiole.*—Length: 4.5–7.0 cm. Diameter: 0.3 cm. Color: Yellow-Green Group 144A.

*Veins.*—Venation type: Palmate. Color: Upper surface: Green Group 137A. Lower surface: Yellow-Green Group 144B.

INFLORESCENCE

Bud:

*Shape of development when bud characteristics determined.*—Bud shows color at side and sepals are just parting at the tips.

*Shape of cluster.*—Elliptical.

*Diameter of cluster.*—2.6 cm.

*Number of buds per cluster.*—4–7.

*Shape of individual bud.*—Elliptical to teardrop shaped.

*Length of individual bud.*—2.0–2.4 cm.

*Width of individual bud.*—0.5–0.7 cm.

Natural flowering season at specified location(s): Will naturally flower under cooler temperatures in California, requires cool temperatures and light to flower in the greenhouse after bud is set.

Blooming habit: 10 weeks under a specific greenhouse regime is needed to set bud.

Umbel diameter: 8.0–9.5 cm.

Umbel depth: 6.0–6.5 cm.

Borne: Umbel, flowers on pedicel, pedicel on peduncle.

Inflorescence position: Above foliage.

Number of inflorescences per lateral branch: 2–4.

Lastingness of an individual flower: 7–10 days.

Florets:

*Form.*—Cupped.

*Number per umbel.*—3–7.

*Diameter.*—4.8–5.0 cm.

*Depth.*—3.6–3.8 cm. from petal attachment to highest presentation.

Petals:

*Color.*—Upper surface: Lower petals without pronounced 'eye' are Red-Purple Group 71B. They are highly reflective with a blotch of Red-Purple Group 59B near the center and flowering to petal base. Dark veining is described as Greyed-Purple Group 187A from base to where eye margin ends. Petal base is Red-Purple Group 74D. Upper petals with eye are similar to the lower petals; however, the eye 'blotch' is larger and darker Red-Purple Group 59A. Veins feather to outside of the petal at the base tip to the end of the bottom ⅓ of the petal. The veins are Greyed-Purple Group 187A. The base is White Group 155D with Red-Purple Group 71C bleeding into it. Lower surface: Red-Purple Group 59B with Red-Purple Group 59A veining. At the base, lighter shades appear.

*Shape.*—Inverted teardrop.

*Length.*—Upper two petals, 3.7 cm.; Lower three petals, 3.2 cm.

*Width.*—Upper two petals, 3.0 cm.; Lower three petals, 2.2 cm.

*Apex shape.*—Rounded.

*Base shape.*—Pointed, arrow tip.

*Margin.*—Entire, with a slight ruffled appearance on larger petals.

*Number per floret.*—5 (2 larger, 3 smaller).

*Texture.*—Smooth.

*Tonality from a distance.*—Satiny, reflective of shades of red purple.

Petaloids: None present.

Pedicel:

*Length.*—3.5–4.9 cm.

*Diameter.*—0.2 cm.

*Color.*—Yellow-Green Group 144A.

Peduncle:

*Length.*—5–6.5 cm.

*Diameter.*—0.2 cm–0.25 cm.

*Texture.*—Smooth with slight pubescence.

*Color.*—Yellow-Green Group 144A.

Sepal:

*Number.*—5.

*Pubescence.*—Moderate.

*Shape.*—Lanceolate.

*Width.*—0.4–0.6 cm.

*Length.*—2.0–2.2 cm.

Fragrance: None observed.

Disease resistance: None observed.

Temperature tolerance: None observed.

Drought tolerance: None observed.

REPRODUCTIVE ORGANS

Stamens:

*Number* (*per flower*).—5–9.

*Filament.*—Length: 0.9–1.1 cm. Color: Red-Purple Group 71D and White Group 155D.

*Anthers.*—Shape: Ovate with point at one tip which curls upward. Length: 0.3–0.45 cm. Color: Greyed-Yellow Group 161C.

*Pollen.*—None observed.

Pistils:

*Number.*—1.

*Length.*—2.0–2.1 cm.

*Style.*—Length: 1.7 cm. Color: Red-Purple Group 59B.

*Stigma.*—Shape: Splits into 5 and will curve downward. Color: Red-Purple Group 59A. Size: 0.3–0.4 cm.

*Ovaries.*—Position: Superior. Length: 0.5 cm. Width: 0.25 cm.

I claim:

1. A new and distinct variety of *geranium* plant named 'Elegance Burgundy' as described and illustrated.

* * * * *

UNITED STATES PATENT AND TRADEMARK OFFICE

CERTIFICATE OF CORRECTION

PATENT NO. : PP 17,142 P2
APPLICATION NO. : 11/177058
DATED : October 10, 2006
INVENTOR(S) : Lemon It is certified that error appears in the above-identified patent and that said Letters Patent is hereby corrected as shown below:

Column 3, Line 4, under "Petals", "flowering to petal base" should read -- flowing to petal base --

Signed and Sealed this

Sixth Day of March, 2007

JON W. DUDAS
*Director of the United States Patent and Trademark Office*